United States Patent [19]

Matthews et al.

[11] Patent Number: 5,105,140

[45] Date of Patent: Apr. 14, 1992

[54] PERISTALTIC PUMP MOTOR DRIVE

[75] Inventors: Joseph B. Matthews, Grayslake; George A. Bowman, Vernon Hills, both of Ill.

[73] Assignee: Baxer International Inc., Deerfield, Ill.

[21] Appl. No.: 463,644

[22] Filed: Jan. 11, 1990

[51] Int. Cl.⁵ ............................................. H02P 8/00
[52] U.S. Cl. ..................................................... 318/696
[58] Field of Search ........................ 318/696, 685, 254

[56] References Cited

U.S. PATENT DOCUMENTS

| | | |
|---|---|---|
| 3,746,959 | 7/1973 | Kobayashi et al. . |
| 3,750,000 | 7/1973 | Bruckner et al. . |
| 3,826,966 | 7/1974 | Nagasaka et al. . |
| 4,015,419 | 4/1977 | Morokawa et al. ................. 58/23 R |
| 4,024,447 | 5/1977 | Epstein . |
| 4,107,595 | 8/1978 | Campe . |
| 4,140,955 | 2/1979 | Drabing . |
| 4,254,491 | 3/1981 | Haub et al. . |
| 4,361,410 | 11/1982 | Nakajima et al. . |
| 4,380,722 | 4/1983 | Oltendorf ............................ 318/696 |
| 4,381,481 | 4/1983 | Kuppers et al. ..................... 318/696 |
| 4,420,717 | 12/1983 | Wallace et al. . |
| 4,467,256 | 8/1984 | Antognini et al. . |
| 4,468,602 | 8/1984 | Antognini et al. . |
| 4,471,283 | 9/1984 | Presley . |
| 4,574,228 | 3/1986 | Blue et al. . |
| 4,587,473 | 5/1986 | Turvey . |
| 4,599,545 | 7/1986 | Moriki et al. ................... 318/599 X |
| 4,600,868 | 7/1986 | Bryant . |
| 4,604,034 | 8/1986 | Wheeldon et al. . |
| 4,642,544 | 2/1987 | Furumura et al. . |
| 4,647,829 | 3/1987 | Giguere et al. . |
| 4,680,524 | 7/1987 | Do et al. . |
| 4,707,640 | 11/1987 | Bose . |
| 4,751,445 | 6/1988 | Sakai ................................. 318/696 |
| 4,757,245 | 7/1988 | Ayers et al. ........................ 318/685 |
| 4,760,320 | 7/1988 | Tsugita ............................. 318/696 |
| 4,772,840 | 9/1988 | Taghezout .......................... 318/696 |

Primary Examiner—Bentsu Ro
Attorney, Agent, or Firm—Paul E. Schaafsma; Amy L. H. Rockwell; Paul C. Flattery

[57] ABSTRACT

The present invention provides a drive signal for a peristaltic pump motor. A first circuit is provided which generates a first series of pulses at a given frequency. A second circuit is provided which generates a second series of pulses having a frequency higher than the frequency of the first series of pulses. A third circuit is provided which generates a third series of pulses having a frequency between the frequency of the first and second series of pulses. Finally, a circuit is provided which combines the three series of pulses into a drive signal. The drive signal length is determined by the frequency of the first series of pulses. The drive signal further is divided into two sections, an initial pulse stage determined by the frequency of the third series of pulses, and a modulated pulse stage being a series of pulses determined by the frequency of the second series of pulses.

20 Claims, 10 Drawing Sheets

PERISTALTIC PUMP MOTOR DRIVE

FIELD OF THE INVENTION

The present invention relates in general to a peristaltic pumping apparatus and in particular to a motor driving means for peristaltic pumps.

BACKGROUND OF THE INVENTION

Administration of intravenous fluids to a patient is well known in the art. Typically, a solution such as saline, glucose or electrolyte in a glass or flexible container is fed to a patient's venous access site via a length of flexible plastic tubing such as polyvinyl chloride (PVC) tubing. The rate of flow of the fluid is controlled by a roller clamp which is adjusted to restrict the flow lumen of the tubing until the desired flow rate is obtained.

Flow from the container to the patient may also be regulated by means other than a roller clamp. It is becoming more and more common to use an electronically controlled pump. One type of pump that is used for intravenous fluid administration is a peristaltic-type pump.

Use of peristaltic pumping action is particularly well suited for the medical field. This is because peristaltic pumping action can be applied externally of the tubing carrying the intravenous fluid. This maintains the sterile condition of the intravenous fluid within the tubing while imparting fluid propulsion on the fluid. The peristaltic pumping action can also be applied at any point on the tubing.

In a common type of peristaltic pump used in the medical field, a driving motor is connected to an array of cams angularly spaced from each other. The cams in turn drive cam followers which are connected to corresponding pressure fingers. These elements cooperate to impart a linear wave motion on the pressure fingers. A pressure plate is secured juxtaposed to and spaced from the pressure fingers. The pressure plate holds the tubing against the reciprocating pressure fingers to impart the wave motion on the tubing to propel the fluid. Alternatively, the driving motor drives a rotary-type peristaltic pump in which a plurality of rollers contact the tubing to impart fluid propulsion. A pressure plate holds the tubing adjacent to the rollers.

In a preferred embodiment of peristaltic pumps, the driving motor is a stepping motor which rotates in small increments or steps. While a stepping motor rotating at a high rate of speed gives a visual impression that the rotation is constant, the stepping motor in fact turns through a series of small angular increments or steps which are followed by a brief period of rest. In stepping motors utilized in peristaltic pumps in the medical field, these small angular steps can range from about 0.36° to 7.2° and in a preferred embodiment are about 1.8°. This results in a series of steps of the shaft between 1000 and 50 per revolution or, in the preferred embodiment, about 200 steps per revolution.

In these prior art devices, the stepper motor was driven conventionally to impart the fluid propulsion on the pressure fingers or rollers. A drawback in such devices is the use of a large amount of power which resulted in use of large power sources such as batteries and a limited infusion time.

Additionally, different drive methods are also preferably utilized which are commonly referred to as wave drive, half step drive, and full step drive. In this prior art, these different step driving signals were the only possible driving methods available to effectuate a coordination of power control to provide measuring motor torque.

Further, in pumps of the prior art, the power feeding the driving motor needed to be reduced by absorptive lumped or active elements or was reduced by adjusting the voltage to the motor using a feedback microprocessing means.

What would thus be desirable is a peristaltic pumping apparatus in which a wide variety of stepping frequencies and a new inventive modulation means be provided in an efficient manner to provide a very wide range of infusion rates, including microinfusion. It would further be desirable for the peristaltic pumping apparatus to reduce the amount of power needed to drive the stepping motor without using absorptive or lumped elements. It would be still further desirable for the peristaltic pumping apparatus to automatically provide instantly and safely the required power compensation to the stepping motor. The present invention provides such a device.

SUMMARY OF THE INVENTION

The present invention provides a drive signal for a peristaltic pump motor. A first circuit is provided which generates a first series of pulses at a given frequency. A second circuit is provided which generates a second series of pulses having a frequency higher than the frequency of the first series of pulses. A third circuit is provided which generates a third series of pulses having a frequency between the frequency of the first and second series of pulses. Finally, a circuit is provided which combines the three series of pulses into a drive signal. The drive signal length is determined by the frequency of the first series of pulses. The drive signal further is divided into two sections, an initial pulse stage determined by the frequency of the third series of pulses, and a modulated pulse stage being a series of pulses determined by the frequency of the second series of pulses.

In an additional embodiment of the present invention, additional circuit means are provided for synchronizing the first series of pulses and the second series of pulses. Additionally, the third circuit means utilizes the first series of pulses to generate the third series of pulses thereby assuring synchronization of all the pulses.

In an additional preferred embodiment, additional circuit means are provided for monitoring the power consumption of the driving motor, the monitoring means being in communication with a microprocessor, the microprocessor adjusting the drive signal as a function of the power consumption of the driving motor.

DESCRIPTION OF A PREFERRED EMBODIMENT

Figure 1:
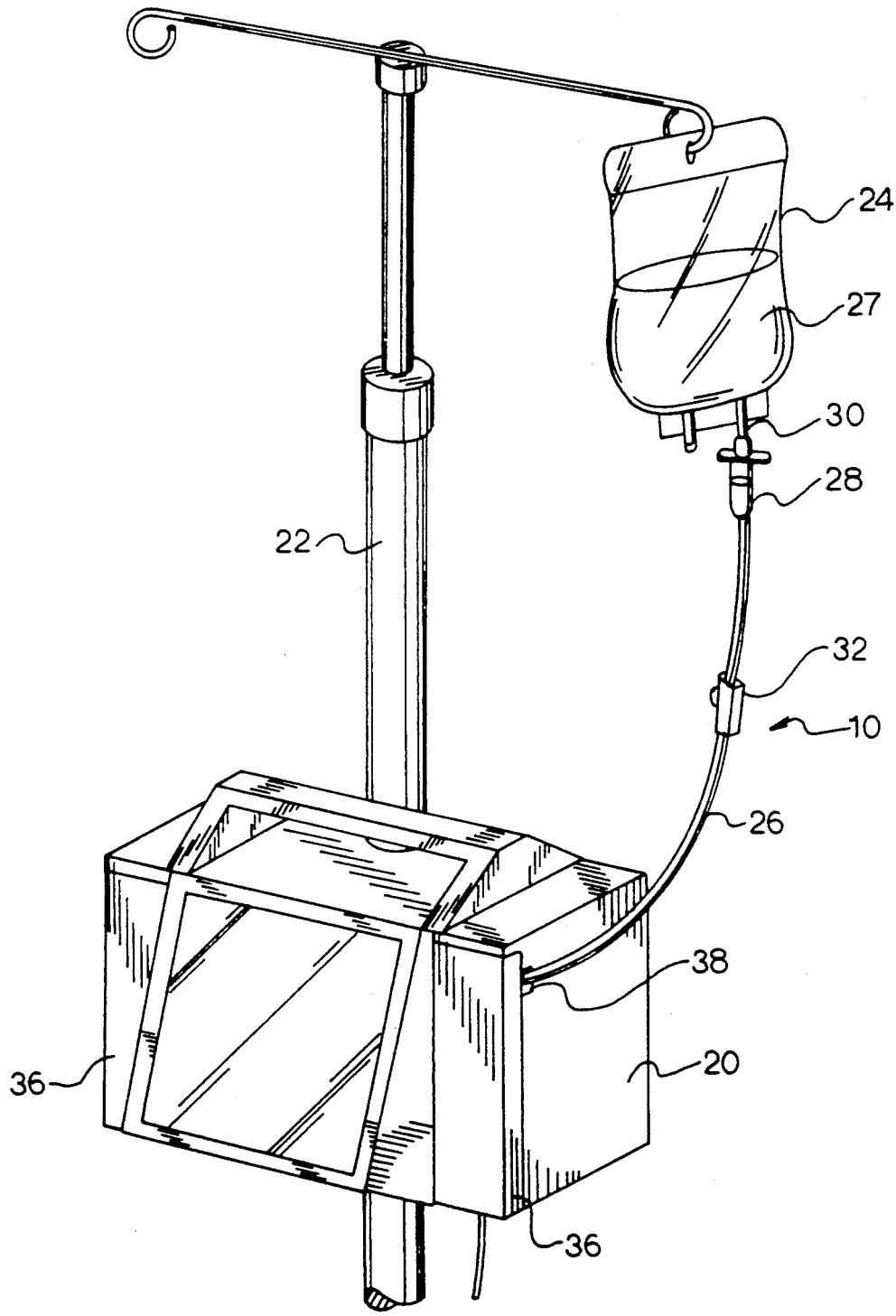
FIG. 1 is a perspective view of an intravenous pump set utilizing a peristaltic pumping apparatus.

FIG. 1 is an illustration of an intravenous administration set up using a pump and a source of intravenous fluid such as a flexible container. Pump 20, which is provided with a pump operating mechanism and operating electronics (not shown), is mounted on an I.V. stand 22 which also serves as a support for the intravenous fluid container 24. Container 24, which typically contains a fluid 27 such as saline that is continually administered, is also suspended from stand 22.

An administration set 10 provides a flow path from container 24 to the patient via pump 20. Set 10 includes a segment of flexible plastic tubing 26 such as polyvinyl chloride (PVC) tubing.

Tubing 26 at its proximal end is attached to a drip chamber 28 that in turn is attached via a spike (not shown) to an outlet port 30 of container 24. A clamping means such as a roller clamp 32 is positioned on tubing 26 at a point between pump 20 and container 24. Tubing 26 has connected at its distal end means for connecting set 10 to a vein access device, such as a catheter or needle (not shown).

Pump 20 includes a hinged door 36 which covers the peristaltic pumping apparatus hardware. To set up pump 20, door 36 is opened, tubing 26 is inserted into the peristaltic pumping apparatus as described in detail below, door 36 is closed, and pump 20 is activated. The pump 20 also defines apertures 38 at the upper and lower (not shown) peripheries of the door 36 through which the tubing 26 extends when door 36 is closed. While the embodiment depicted in FIG. 1 includes a dual drive peristaltic pump, the present invention contemplates use of any number of pump drives in a single peristaltic pump.

Figure 2:
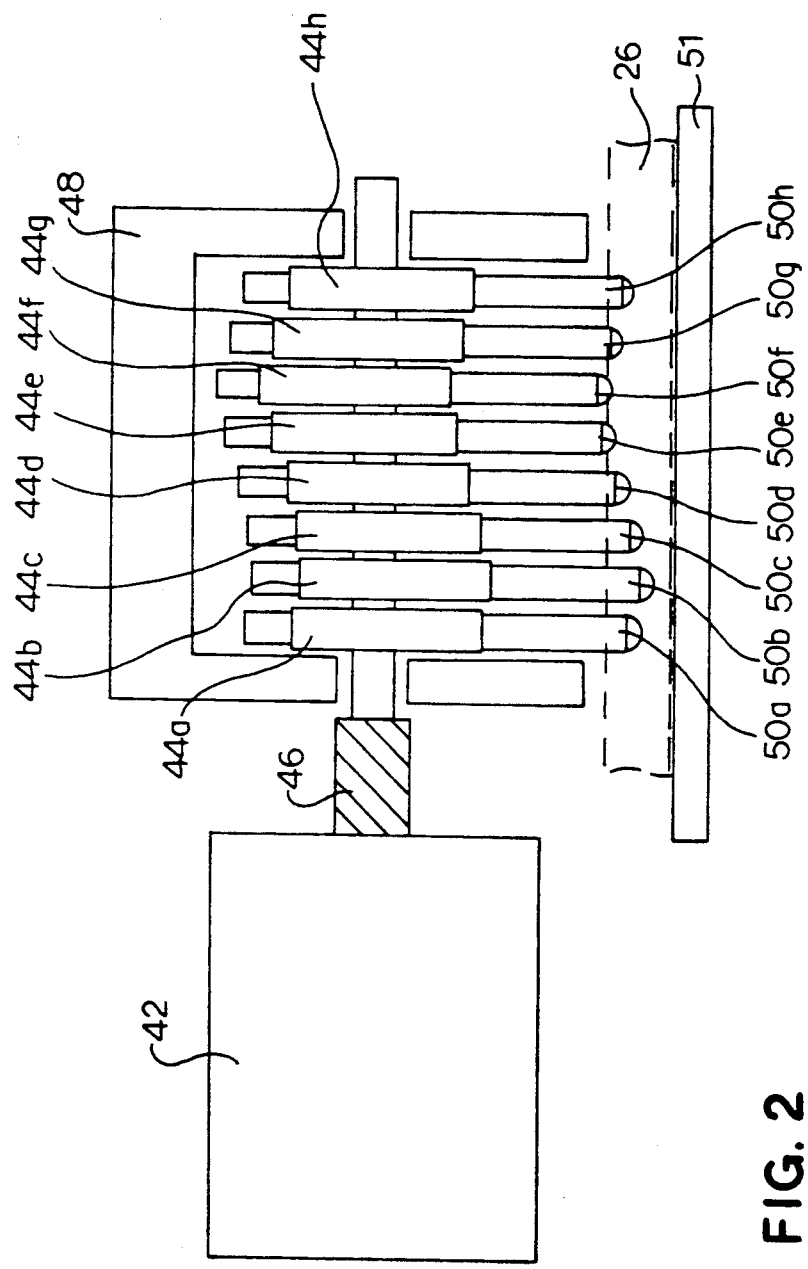
FIG. 2 is a schematic of a peristaltic pumping apparatus.

Referring to FIG. 2, a general schematic of a peristaltic pumping apparatus is seen. A driving motor 42 is connected to a plurality of cams 44a-h via a drive shaft 46. Each cam 44 is angularly displaced from the adjacent cam. The plurality of angularly displaced cams 44a-h are journaled in housing 48 which enables rotation in conjunction with the drive shaft 46.

A plurality of reciprocating pressure fingers 50a-h are provided, the number of which corresponds to the number of cams 44. Each pressure finger 50 cooperates with a corresponding cam 44 by acting as a cam follower to reciprocally drive the pressure finger 50. The rotational movement of the drive shaft 46 is thus converted into a linear wave movement of the plurality of reciprocating pressure fingers 50a-h.

A pressure plate 54 is provided located juxtaposed to the pressure fingers 50a-h and extending parallel to the axis of the cams. Tubing 26 is contained between the pressure fingers 50 and the pressure plate 54. Fluid propulsion is effectuated by the pressure fingers 50a-h squeezing the tubing 26 in the linear wave movement imparted by the angular orientation of the cams 44a-h.

Figure 3:
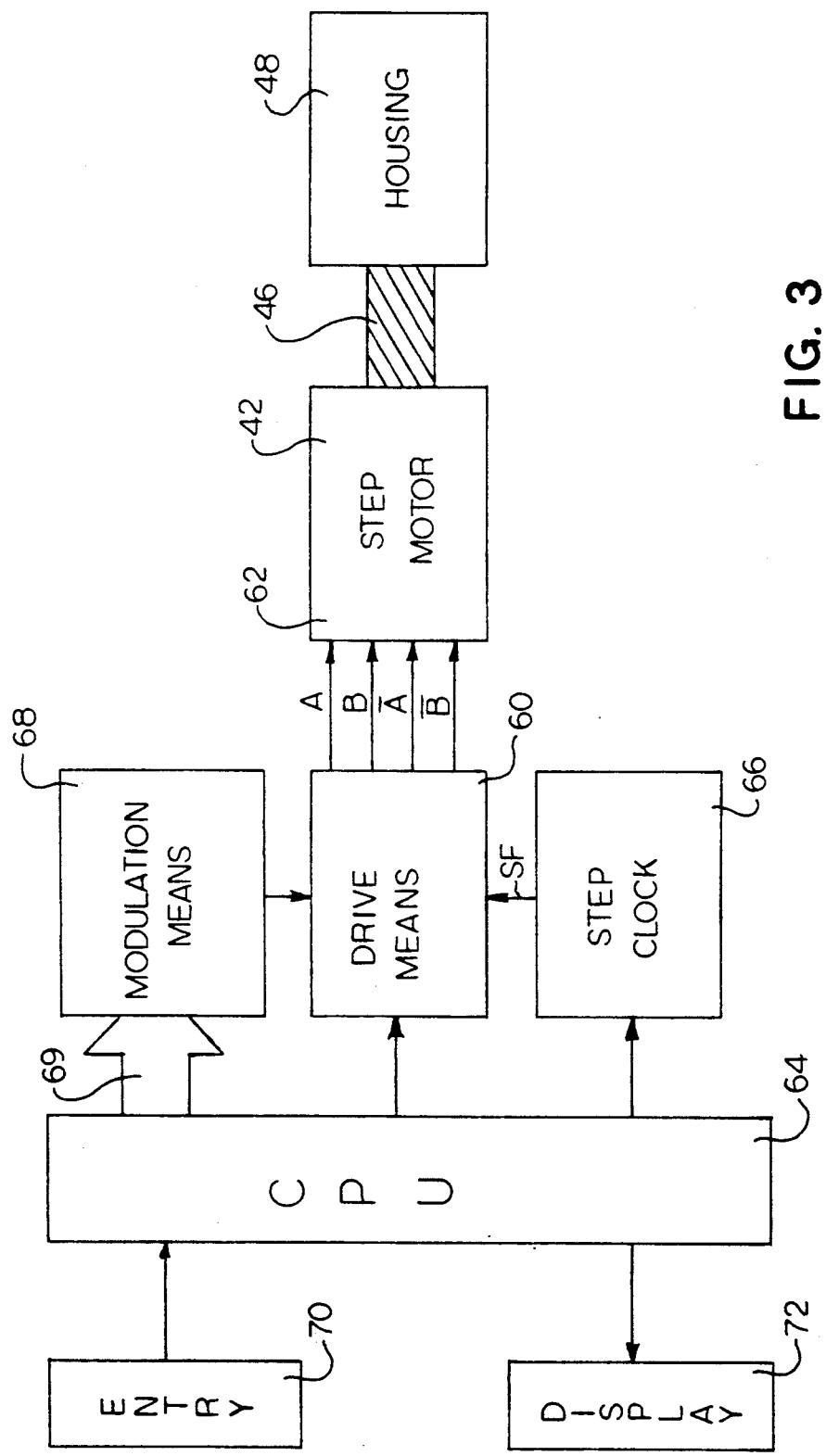
FIG. 3 is a block diagram of the operating electronics of a peristaltic pumping apparatus made in accordance with the principles of the present invention.

Referring now to FIG. 3, a schematic of a preferred embodiment of a device in accordance with the principles of the present invention is seen. As previously seen, the pumping mechanism is provided in housing 48. The pumping mechanism is driven by driving motor 42 via drive shaft 46. The driving motor 42 is a stepping motor which can preferably have 200 steps per revolution and a four step cycle. The stepping motor 42 is driven by drive means 60 which generates four signals A, B, $\overline{A}$, $\overline{B}$ to drive the stepping motor 42. Interfaced between the drive means 60 and the stepping motor 42 are power monitoring means 62 which monitor the power consumption of the stepping motor 42.

The drive means 60 is set by input from a central processing unit 64. The central processing unit 64 also inputs into a step clock 66, the output of which is inputted into the driving means 60. The step clock 66 provides means for generating a step clock signal SF which is utilized by the drive means 60 as discussed in detail below.

A modulation means 68 for modulating the drive signal to conserve power is also provided. The modulation means 68 is set by the central processing unit 64 over data bus 69. Various infusion parameters are inputted into the central processing unit 64 by the user via an entry keyboard 70 while a display 72 is preferably provided to display information such as infusion rate.

Figure 4:
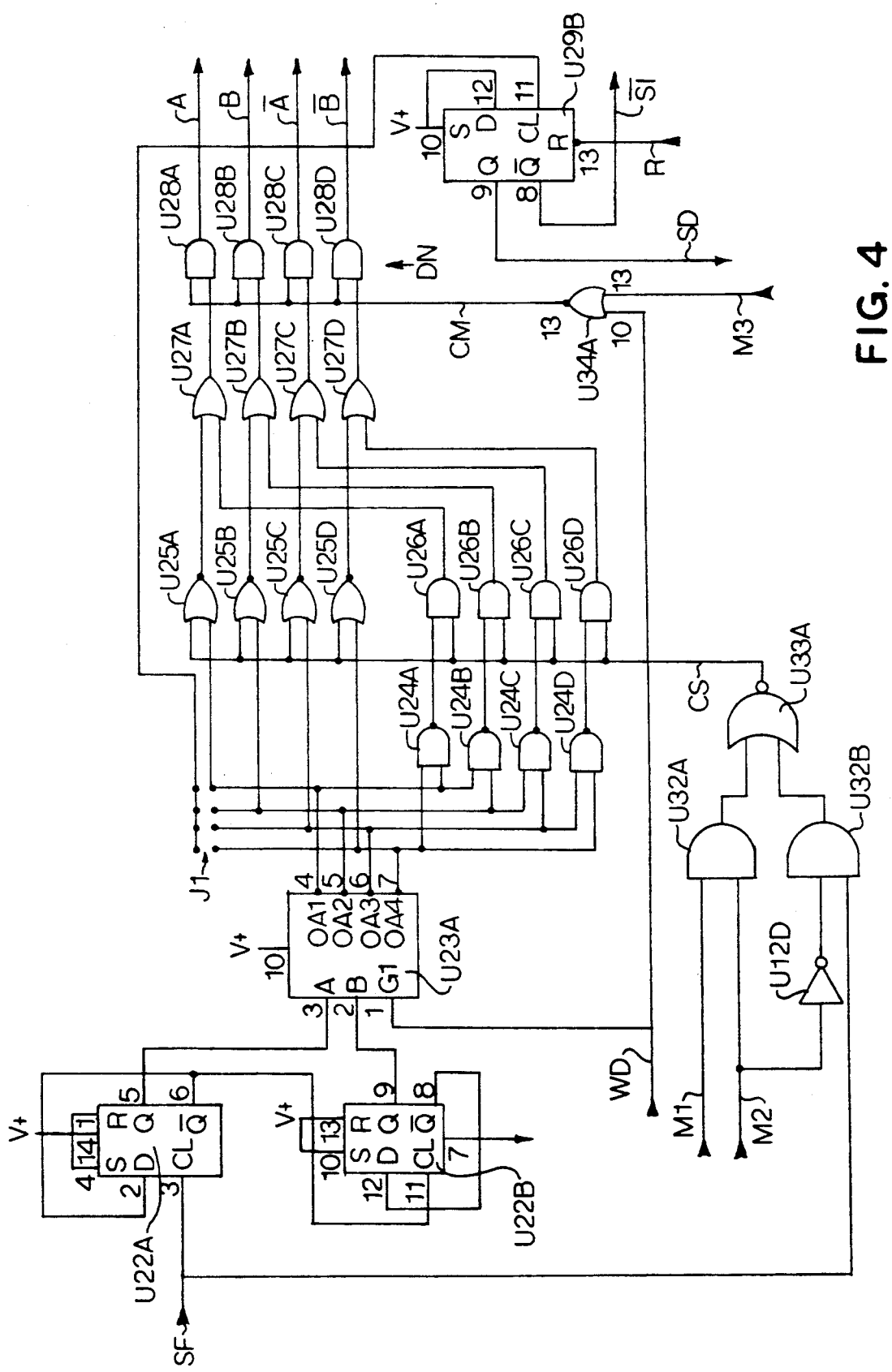
FIG. 4 is a circuit diagram of a motor drive means in accordance with the principles of the present invention.

Referring to FIG. 4, a preferred embodiment of the motor phase driving means is seen. A pair of edge triggered flip-flop dividers U22A, U22B are provided which can be embodied in an integrated chip such as a type 74HC74. The first divider U22A has as a clock input CL the step clock SF output of the timing means. The inverted output $\overline{Q}$ of the first divider U22A is connected both to the data input D of that divider U22A as well as the clock input CL of the second divider U22B.

The inverted output $\overline{Q}$ of the second divider U22B is inputted into the data input D of that divider U22B. The preset S and clear R inputs of both dividers U22A, U22B are connected to a power supply V+. The non-inverted output Q of the first divider U22A is connected to a multiplexer integrated chip U23A such as a type HCT 139 IC via one-select input A. The non-inverted output Q of the second select divider U22B is also inputted into the multiplexer U23A via second select input B. A watchdog signal WD is inputted into the gate enable input G1 of multiplexer U23A to safely disable the motor and modulation system when watchdog signal WD goes to a high state.

The multiplexer outputs $O_{A1}$, $O_{A2}$, $O_{A3}$, $O_{A4}$ are connected to a signal generating means. Specifically, in a preferred embodiment, multiplexer output $O_{A1}$ is inputted into a first NAND gate U24A, a second NAND gate U24B, and a first NOR gate U25A. Multiplexer output $O_{A2}$ is also inputted into the second NAND gate U24B as well as a third NAND gate U24C and a second NOR gate U25B. Multiplexer output $O_{A3}$ is also inputted into the third NAND gate U24C as well as a fourth NAND gate U24D and a third NOR gate U25C. Multiplexer output $O_{A4}$ is also inputted into the first NAND gate U24A and the fourth NAND gate U24D as well as a fourth NOR gate U25D.

The output of the first NAND gate U24A is inputted into a first AND gate U26A. The output of the second NAND gate U24B is inputted into a second AND gate U26B. The output of the third NAND gate U24C is inputted into a third AND gate U26C. The output of the fourth NAND gate U24D is inputted into an fourth AND gate U26D.

A control signal CS is inputted into the first, second, third and fourth NOR gates U25A, U25B, U25C, U25D and to the first, second, third, and fourth AND gates U26A, U26B, U26C, U26D. The control signal CS is generated by user controlled inputs M1 and M2. Inputs M1, M2 are inputted into a fifth AND gate U32A while input M2 is also inverted by an inverter U12D and inputted into a sixth AND gate U32B. The step clock SF is also inputted into this sixth AND gate U32B. The outputs of AND gates U32A, U32B are inputted into a fifth NOR gate U33A, the output of which comprises control signal CS. Thus, when M1 and M2 are set high, the control signal CS is low; when M1 is low and M2 is high, the control signal CS is high; when M1 is high and M2 low, the control signal CS alternates as an inverse function of step clock SF.

The outputs of the first NOR gate U25A and the first AND gate U26A are inputted into a first OR gate U27A. The outputs of the second NOR gate U25B and the second AND gate U26B are inputted into a second OR gate U27B. The outputs of the third NOR gate U25C and the third AND gate U26C are inputted into a third OR gate U27C. The outputs of the fourth NOR gate U25D and the fourth AND gate U26D are inputted into a fourth OR gate U27D.

The output of the first OR gate U27A is inputted into a seventh AND gate U28A. The output of the second OR gate U27B is inputted into an eighth AND gate U28B. The output of third OR gate U27C is inputted into a ninth AND gate U28C. The output of the fourth OR gate U27D is inputted into a tenth AND gate U28D.

The seventh, eighth, ninth and tenth AND gates U28A, U28B, U28C, U28D also have as input a control/disable signal CM. The outputs of the seventh, eighth, ninth, and tenth AND gates U28A, U28B, U28C, U28D are the drive signals A, B, $\overline{A}$, $\overline{B}$ respectively. Control/disable signal CM is generated by a NOR gate U34A having as inputs the watchdog signal WD and a first modulation signal M3. When the watchdog signal WD is in its normally low state, control/disable signal CM is an inverse function of modulation signal M3 while a high watchdog signal WD results in a low control/disable signal CM. Thus, in the instance of a high watchdog signal WD, the seventh, eighth, ninth and tenth AND gates U28A, U28B, U28C, U28D act as a disabling network means DN.

Finally a phase selection circuit for the phase selection means is provided. In a preferred embodiment, the phase selection circuit means includes a third divider integrated chip U29B which may also be type 74HC74. The data input D and the preset input S of divider U29B are connected to a power supply V+. The clock input CL is connected to a predetermined phase line via a jumper J1. The non-inverted output Q is a high going signal SD which is inputted into microprocessor for signifying that the microprocessor should read an encoder wheel on this pump channel. An example of such an encoder wheel is disclosed in U.S. patent application Ser. No. 463,716 entitled "PERISTALTIC PUMP MONITORING DEVICE AND METHOD" which is being filed concurrently with this application and which disclosure is incorporated herein. The inverted output $\overline{Q}$ is a low going signal ST which is inputted into the microprocessor for interrupting the microprocessor for servicing the encoder wheel on any one of a plurality of pump channels. After servicing, the processor resets divider U29B via a reset pulse inputted into clear input R.

As an alternative construction, the detection of the phase selection clock input CL, via jumper J1, may be made by the microprocessor alone. In that instance, jumper J1 would be connected permanently to signal $O_{A1}$ and the microprocessor would select an offset number of steps equivalent to the difference between phase $O_{A1}$ and the true phase when the encoder wheel revolution optical path becomes transparent.

Referring now to FIG. 8 in conjunction with FIG. 4, the operation of the motor phase driving means will be described. Initially, the step clock signal SF is provided to the first divider U22A as indicated by FIG. 8A. Divider U22A outputs a divided step clock signal SF as seen in FIG. 8B. This signal is again divided by divider U22B, which results in an output seen in FIG. 8C.

The divided signal outputs from dividers U22A and U22B are inputted into multiplexer U23A. Multiplexer U23A outputs four signals, $O_{A1}$, $O_{A2}$, $O_{A3}$, $O_{A4}$, seen in FIG. 8D, one of which is inputted into the phase selection means.

In order to provide a wave drive or a one phase excitation mode, input signals M1 and M2 are set high by microprocessor. As previously seen, this results in a control signal CS constant low output from NOR gate U33A. Additionally, the watchdog signal WD is assumed low for this description.

With a low control signal CS provided to AND gates U26A–U26D and NOR gates U25A–U25D, and the output of AND gates U26A–U26D as supplied to OR gates U27A–U27D is also low. As such, when multiplex output $O_{A1}$ is high, a high signal and a low signal are provided to NOR gate U25A, which results in a low output from NOR gate U25A being provided to OR gate U27A, which results in a low output from OR gate U27A which is passed by disabling network DN which results in a low A output. When multiplexer output $O_{A2}$ is low, a low signal and a low signal are provided to NOR gate U25A which results in a high output from NOR gate U25A being provided to OR gate U27A which results in a high output from OR gate U27A, which results in a high A output.

Likewise, when multiplexer output $O_{A2}$ is high, a low B output results while when multiplexer output $O_{A2}$ is low, a high B output results; when multiplexer output $O_{A3}$ is high, output C is low and when output $O_{A3}$ is low, output C is high; when multiplexer output $O_{A4}$ is high, output D is low while when output $O_{A4}$ is low, output D is high. Wave drive or one phase excitation mode output can be seen in FIG. 8E.

When input M1 is set to low and input M2 is set to high, a full step drive or a two phase excitation mode is provided. As previously seen, this results in a control signal high output from NOR gate U33A. This also results in a low signal from NOR gates U25A–U25D. Thus, both AND gates U26A–U26D and OR gates U27A–U27D act to pass the output of NAND gates U24A–U24D.

Thus, at NAND gate U27A, a low output from either multiplexer output $O_{A1}$ or $O_{A4}$ results in a high A output while a high output from both multiplexer outputs $O_{A1}$ and $O_{A4}$ results in a low A output. Likewise, low outputs from multiplexer $O_{A1}$ or $O_{A2}$ output results in a high B output while a high $O_{A1}$ or $O_{A2}$ output results in a low B output; a low $O_{A2}$ or $O_{A3}$ output results in a high A output while a high $O_{A2}$ and a high $O_{A3}$ output results in a low A output; a low $O_{A3}$ or $O_{A4}$ output results in a high B output while a high $O_{A3}$ and a high $O_{A4}$ output results in a low B output. Full step drive or two phase excitation mode output can be seen in FIG. 8F.

When input M1 is set high while input M2 is set low, a half step drive or one-two phase excitation mode is provided. As previously seen, this results in a control signal CS from NOR gate U33A as an inverse of step clock output SF.

Thus, in the half step drive mode, when $O_{A1}$ is low while $O_{A2}-O_{A4}$ are high, NAND gate U24A outputs a high signal to AND gate U26A, NAND gate U24B outputs a high signal to AND gate U26B, NAND gate U24C outputs a low signal to AND gate U26C, and NAND gate U24D outputs a low signal to AND gate U26D. AND gates U26A and U26B act to pass the inverted step clock signal or control signal CS to OR gates U27A and U27B while AND gates U26C and U26D supply a low signal to OR gates U27C and U27D. The low signal $O_{A1}$ supplied to NOR gate U25A acts to invert the control signal CS resulting in the originally phased step clock signal SF being supplied to OR gate U27A while the signals $O_{A2}$, $O_{A3}$ and $O_{A1}$ supplied to NOR gates U25B-U25D result in a low signal supplied to OR gates U27B-U27D.

OR gate U27A is inputted both with a step clock signal SF via NOR gate U25A and the control signal CS via AND gate U26A, resulting in a high A signal. Similarly, output signal B results from the output of OR gate U27B which is supplied with a low signal from NOR gate U25B and an inverted step clock signal from AND gate U26B. Signals $\overline{A}$ and $\overline{B}$ are low as a result of the low signals supplied to OR gates U27C and U27D.

When $O_{A1}$ goes high and $O_{A2}$ goes low, with $O_{A3}$ and $O_{A4}$ high, NAND gates U24A and U24D supply AND gates U26A and U26D with low signals which are passed to OR gates U27A and U27D. NAND gate U24B and U24C output high signals to AND gates U26B and U26C, which then act to pass the inverted step clock or control signal CS to OR gates U27B and U27C. A low signal $O_{A2}$ supplied to NOR gate U25B acts to invert the control signal CS resulting in the originally phased step clock signal SF while the high signal supplied to NOR gates U25A, U25C, U25D results in a low signal supplied to OR gates U27A, U27C and U27D.

Thus, OR gates U27A and U27D receive two low signals, resulting in outputs A and $\overline{B}$ being low. OR gate U27B is inputted both with a step clock signal SF via NOR gate U25B and the control signal CS via AND gate U26B, resulting in a high B output, while the output signal $\overline{A}$ results from the output of OR gate U27C which is inputted with a low signal and the inverted step clock or control signal CS from AND gate U26B.

Figure 8A:
FIG. 8a-8h are graphs showing various signals of the device of the present invention.
Figure 8B:
Figure 8C:
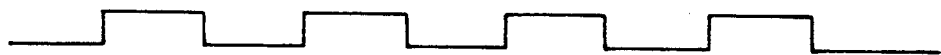
Figure 8D:
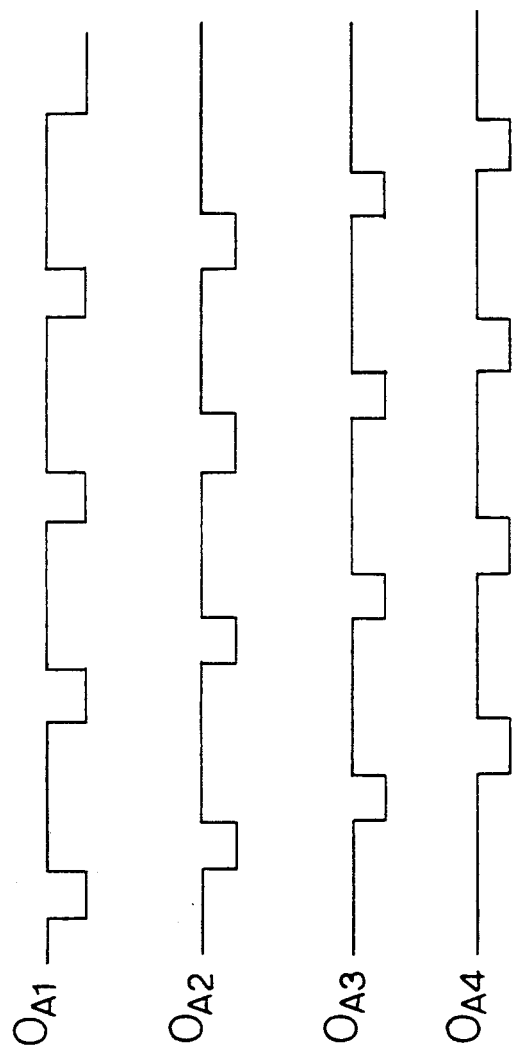
Figure 8E:
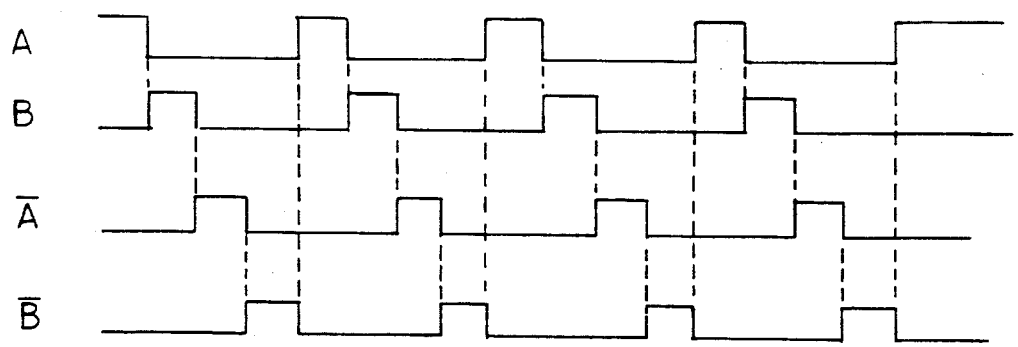
Figure 8F:
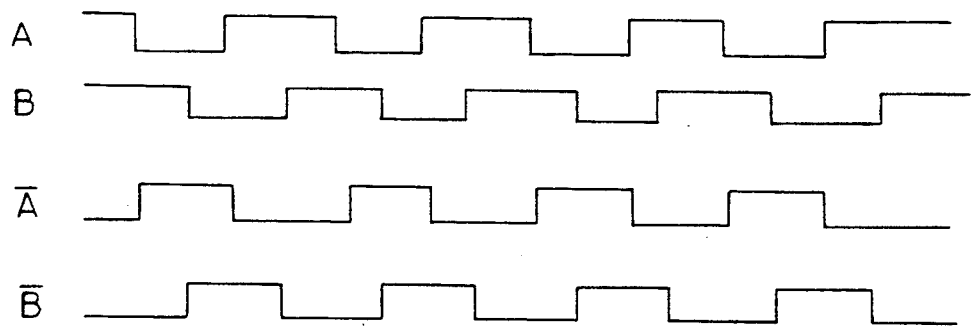
Figure 8G:
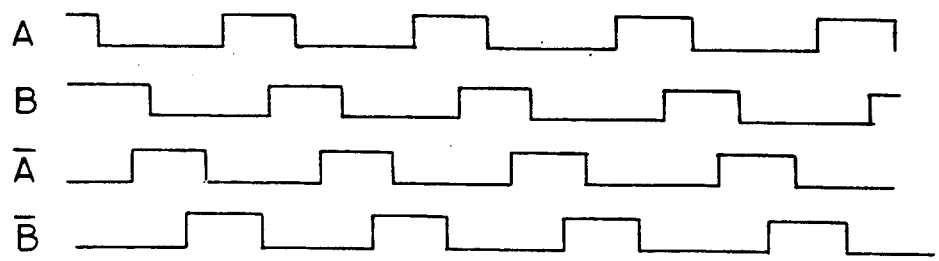

This same pattern is repeated for the remaining phase outputs with a resulting half step drive signal output as seen in FIG. 8G.

Figure 5:
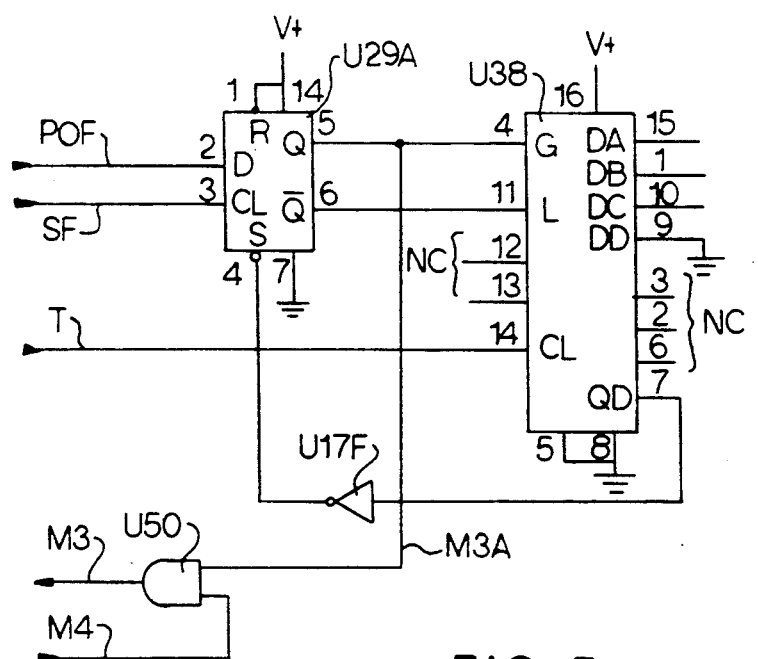
FIG. 5 is a circuit diagram of modulation means in accordance with the principles of the present invention.

Referring now to FIG. 5, preferred embodiments of the circuit means for generating the first modulated signal and the composite modulated signal are seen. An edge triggered flip-flop divider U29A is provided which can be embodied in an integrated chip such as a type 74HC74 and a synchronous binary counter U38 which can be embodied in an integrated chip such as a type 74HC191.

The step clock SF is provided as input to the divider U29A clock input CL. An enable, pulse on/off signal POF which originates from the microprocessor is inputted into the data input D of divider U29A for the purpose of enabling or disabling the modulation. The non-inverted output Q of divider U29A is inputted into the enable input G while the inverted output $\overline{Q}$ of divider U29A is inputted into the load input L of counter U38.

A secondary clock signal T is provided into the clock input CL of counter U38. Counter output $Q_D$ is inverted by an inverter U17F, the inverted output of which is inputted into the preset input S of divider U29A. The reset input R of divider U29A is connected to a power supply V+ while the up/down selection pin 5 of counter U38 is grounded to select up counting. The counter is set via counter select inputs $D_A-D_D$.

The non-inverted output Q of divider U29A, which is the first modulated signal M3A, is inputted into an AND gate U5D. A second modulated signal M4 is also inputted into AND gate U5D. The output of AND gate U5D is the composite modulated signal M3 which is inputted into the motor drive means as previously described and is a composite of both modulated means described.

Figure 8H:
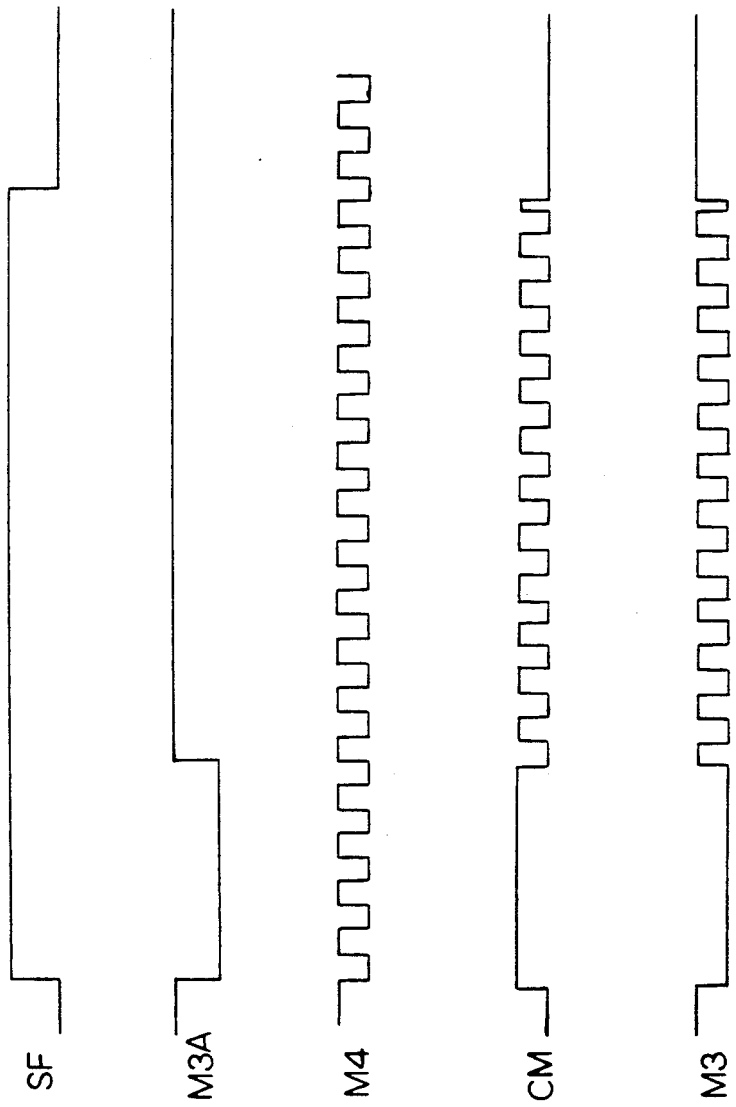

In operation, the enable pulse on/off signal POF either enables divider U29A if low or disables divider U29A if high. If enabled, when the step clock SF signal goes low, the non-inverted output Q goes low which supplies a low signal to AND gate U5D while the inverted output $\overline{Q}$ goes high. This commences counting of the secondary clock input T by the counter U38 from a preset number 0-7, as set by inputs DA, DB and DC, to eight. When 8 is reached, counter output $Q_D$ goes low, which signal is inverted by inverter U17F to high, which is inputted into set input of divider U29A. This causes non-inverted output Q to go high which supplies a high signal AND gate U5D. Non-inverted output Q of divider U29A is the first modulated signal M3A and is thus an inverted pulse signal as seen in FIG. 8H. If second modulation signal M4 is also high, a high composite modulation signal M3 is supplied to the drive pulse means, which when inputted into NOR gate U34A results in a truncated pulse at outputs A, B, $\overline{A}$, $\overline{B}$. This operation repeats itself when the next step pulse occurs. The first modulation means provides sufficient power and torque to align the motor into the next step position.

Figure 6:
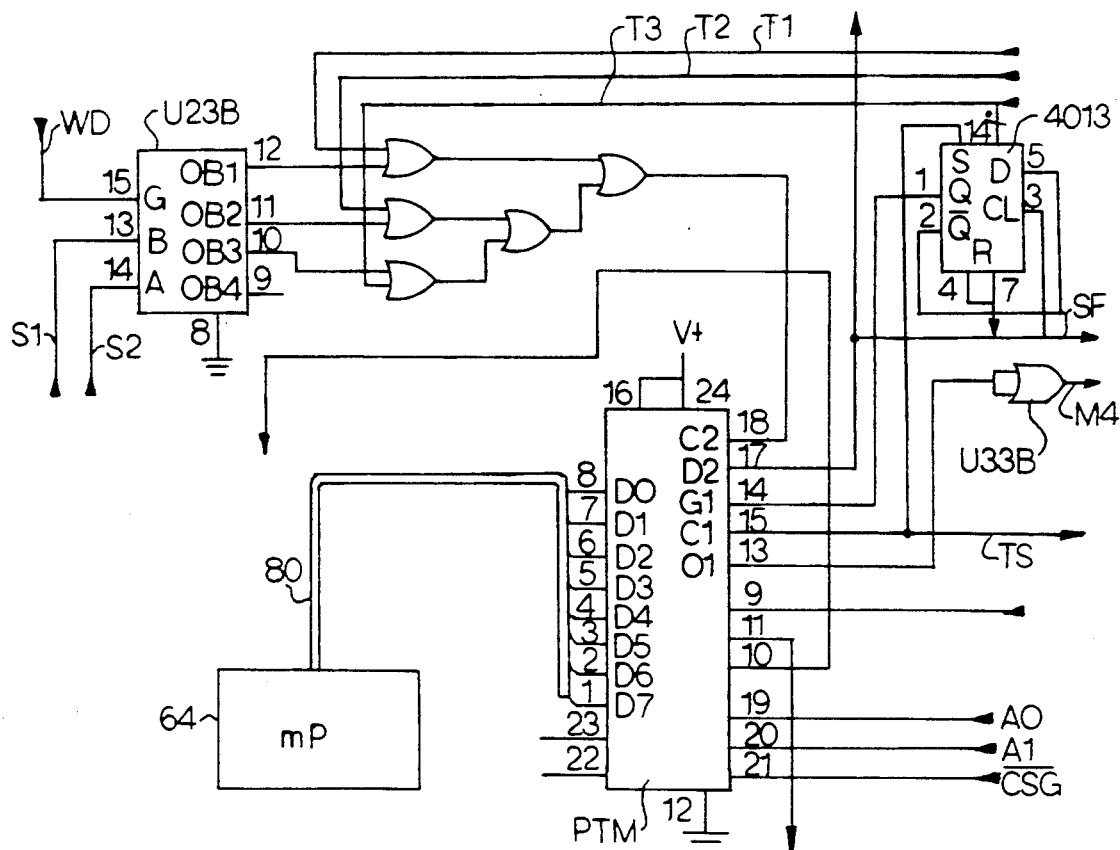
FIG. 6 is a circuit diagram of a second modulation means in accordance with the principles of the present invention.

Referring now to FIG. 6, preferred embodiments of the circuit means for generating the step clock signal and second modulation circuit means M4 are seen.

A multiplexer U23B is provided which can be embodied in an integrated chip such as a type HCT 139. Multiplexer U23B has user generated control signals S1 and S2 as inputs A, B. Watchdog signal WD is provided as a third multiplexer U23B enable input G. When watchdog signal WD is high, the modulation system is safely disabled.

Multiplexer output $O_{B1}$ is inputted into a first NOR gate U30A, multiplexer output $O_{B2}$ is inputted into a second NOR gate U30B, and multiplexer output $O_{B3}$ is inputted into a third NOR gate U30C. Three external clock signals $T_1$, $T_2$, $T_3$ are provided in order to set the very wide step frequency range of operation of the device. Clock signal $T_1$ is inputted into NOR gate U30A, clock signal $T_2$ is inputted into NOR gate U30B and clock signal $T_3$ is inputted into NOR gate U30C.

The outputs of NOR gates U30B and U30C are inputted into an OR gate U31B. The output of OR gate U31B is inputted into a second OR gate U31A as is the output of NOR gate U30A. The output of OR gate U31A is inputted into a counter means.

In a preferred embodiment. a programmable timer module PTM, type 82C54 having three counters is utilized as the counter means. One counter is utilized for developing the step clock signal SF, one counter is utilized for the second modulation means, and the final counter is used in, for example, occlusion detection known in the art.

As such, OR gate U31A output is inputted into PTM clock input two C2. When watchdog signal WD is in a low state, input signals S1 and S2 in conjunction with multiplexer U23B select the desired frequency from the external clock inputs to be inputted to the counter PTM at input C2. The counter PTM is set via input provided at PTM data inputs D0-D7 from a microprocessor 64 via data bus 80 as known in the art. In a preferred embodiment, a type 80C32 microprocessor available from Matra Harris Semi-Conductor Corporation, 2840-100 San Tomas Expressway, Santa Clara, Calif. 95051, is utilized as the microprocessor 64. Clock input C2 is thus divided by the number predetermined in the counter PTM. loaded by the microprocessor and outputted at the counter PTM second output D2 as step clock SF.

The step clock SF output is inputted into a synchronization means. In a preferred embodiment, this means includes a divider integrated circuit 4013. The step clock is inputted into the clock input CL of divider 4013. The inverted output $\overline{Q}$ of the divider 4013 is fed into the data input D while the clear input R is grounded. Preset input S is connected to a sync clock signal Ts which is also inputted into the counter PTM first clock input C1. Divider non-inverted output Q is inputted into the counter PTM first gate input G1.

In operation, when step clock SF goes high. one cycle of the sync clock signal Ts at a much higher frequency is passed by divider 4013 to the gate input G1 of counter one.

This pulse input, which appears as a very narrow negative pulse, commences the counting of counter PTM first clock input line C1 at the microprocessor selected count. When the preprogrammed count is completed, counter PTM first output $0_1$, is predeterminately selected to create a square wave at NOR gate U33B. The inverted square wave at NOR gate U33B output is the second modulated signal M4. The purpose of the second modulated signal M4 is to provide torque to hold the motor in its present stepped state and to prevent an under-damped vibration from occurring.

The second modulated signal M4 can be seen in FIG. 8H. The sync signal assures that both the step frequency SF and second modulated signal M4 are in phase and that the step frequency SF and second modulated signal M4 do not cause a power imbalance in any of the four motor phases. This can be important in reducing motor audible noise.

Referring now to FIGS. 5, 6 and 8, the operation of the modulation circuit means will be described. The second modulated signal M4 is provided to AND gate U5D with the non-inverted output Q of divider U29A or the first modulated signal M3A. Thus, the composite modulated signal M3 is the output of AND gate U5D. First modulated signal M3A and composite modulated signal M3 can be seen in FIG. 8H.

The composite modulated signal M3 is supplied to the drive pulse means as inputted into NOR gate U34A as seen in FIG. 4. When the watchdog signal WD is low, NOR gate U34A inverts composite modulated signal M3 to supply control/disable signal CM to disabling network DN which results in a truncated pulse at outputs A, B, $\overline{A}$, $\overline{B}$ having an initial sustained drive pulse as seen in FIG. 8H. If watchdog signal WD is high, the phase signals A, B, $\overline{A}$, $\overline{B}$ are all low regardless of any other inputs.

Figure 7:
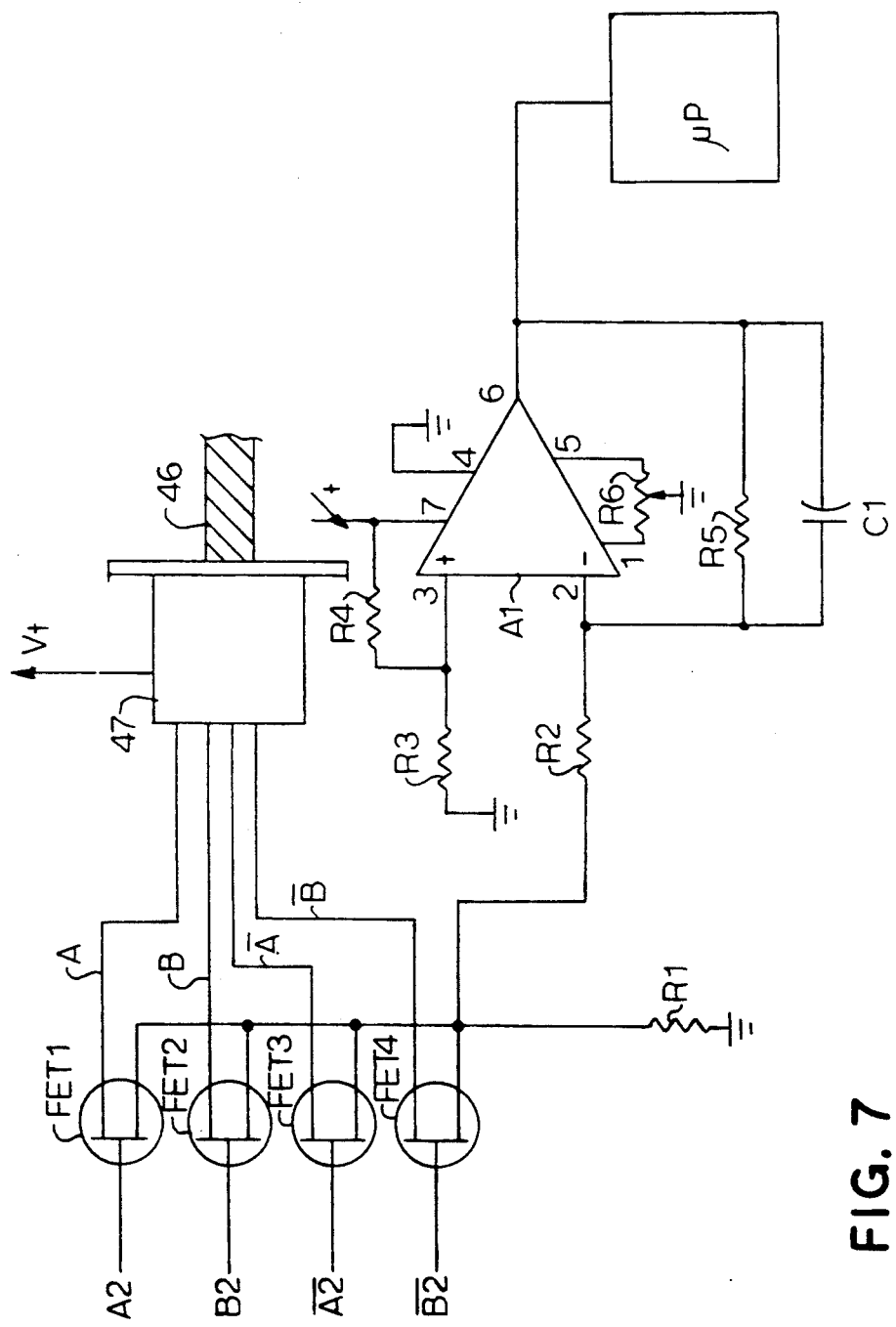
FIG. 7 is a circuit diagram of a power monitor means in accordance with the principles of the present invention.

Referring to FIG. 7, a preferred embodiment of the power monitor means is seen. Drive signals A, B, $\overline{A}$, $\overline{B}$ are inputted into the gates of respective field effect transistors $FET_1$-$FET_4$, which may be type Motorola 12N08, the drains of which are inputted into a type Oriental PX245 motor. A low value resistor R1 is provided between the common source connections 2 of field effect transistors $FET_1$-$FET_4$ and ground.

The junction of the common source connectors 2 of the field effect transistors $FET_1$-$FET_4$ and resistor R1 is fed into the inverting input of an amplifier A1 through resistor R2. The DC offset balance of Amplifier A1 is set via variable resistor R6 while the approximate gain of amplifier A1 is set by the ratio of resistor R5 to resistor R2. Non-inverting input of amplifier A1 such as a Motorola type MC33171 is connected to a power supply V+ by voltage dividing resistors R3, R4. The output of amplifier A1 is fed back into the inverting input through a capacitor C1 and bridged resistor R5 as well as fed into an analog to digital converter which can be contained as a part of the microprocessor 64 or a peripheral integrated circuit such as National ADC0848 or Hitachi 63140.

Thus, the feedback voltage seen at resistor R1 is amplified by amplifier A1 and filtered prior to providing the signal to the analog/digital converter. The analog/digital converter monitors the motor and, if the motor reacts unfavorably or unsafely, adjusts the power to the motor. The system may also monitor its own efficiency and battery life and make adjustments.

It should be understood that various changes and modifications to the preferred embodiments described herein will be apparent to those skilled in the art. For example, the principles of the present medium can also be applied to a rotary type peristaltic pump. Such changes and modifications can be made without departing from the spirit and scope of the present invention and without diminishing its attendant advantages. In particular, both pulse width modulation and frequency modulation are driving modes envisioned as part of the present invention which can alternatively be made possible by adjustments to the controlling software which will be apparent to those skilled in the art. It is, therefore, intended that such changes and modifications be covered by the appended claims.

What is claimed is:

1. A device for modulating a drive signal to drive a motor, comprising:
   a first circuit means for generating a first series of pulses at a given frequency;
   a second circuit means for generating a second series of pulses, the second series of pulses having a frequency higher than the frequency of the first series of pulses;
   a third circuit means for generating a third series of pulses, the third circuit means including a divider means in communication with a counter means, the divider means having as an input the first series of pulses, the third series of pulses having a frequency between the frequency of the first series of pulses and the second series of pulses; and
   means of combining the first, second and third series of pulses to provide the drive signal, the length of the drive signal being determined by the frequency of the first series of pulses, the drive signal further including an initial pulse stage, the length of the initial pulse stage being determined by the frequency of the third series of pulses, the remainder of the length of the drive signal being a series of pulses of the same frequency as the frequency of the second series of pulses.

2. The device of claim 1 wherein the first series of pulses is a step clock signal.

3. The device of claim 1 wherein the first circuit means for generating a step clock signal includes a divider means the input of which is an external clock signal, the output of which is the step clock signal.

4. The device of claim 1 wherein the second circuit means for generating a second series of pulses includes a counter.

5. The device of claim 1 further including means for synchronizing the first series of pulses and the second series of pulses.

6. The device of claim 1 further including means for monitoring the power consumption of the driving motor.

7. The device of claim 1 wherein the second circuit means for generating a second series of pulses includes a counter.

8. A device for modulating a drive signal to drive a motor, comprising:
- a first circuit means for generating a first series of pulses at a given frequency;
- a second circuit means for generating a second series of pulses, the second series of pulses having a frequency higher than the frequency of the first series of pulses;
- a third circuit means for generating a third series of pulses, having a frequency between the frequency of the first series of pulses and the second series of pulses;
- means for synchronizing the first series of pulses and the second series of pulses, the synchronizing means including a divider having as an input the first series of pulses; and
- means for combining the first, second and third series of pulses to provide the drive signal, the length of the drive signal being determined by the frequency of the first series of pulses, the drive signal further including an initial pulse stage, the length of the initial pulse stage being determined by the frequency of the third series of pulses, the remainder of the length of the drive signal being a series of pulses of the same frequency as the frequency of the second series of pulses.

9. The device of claim 8 wherein the third circuit means for generating a third series of pulses includes a divider means in communication with a counter means, the divider means having as an input the first series of pulses.

10. The device of claim 8 wherein the first series of pulses is a step clock signal.

11. The device of claim 8 wherein the first circuit means for generating a step clock signal includes a divider means the input of which is an external clock signal, the output of which is the step clock signal.

12. The device of claim 8 wherein the second circuit means for generating a second series of pulses includes a counter.

13. The device of claim 8 further including means for monitoring the power consumption of the driving motor.

14. The device of claim 13 wherein the means for monitoring the power consumption of the driving motor includes:
- transistor means connected between the combining means and the motor;
- resistive means connected between the transistor means and ground;
- amplifying means having an input connected to the junction of the transistor means and the resistive means and an output connected to a microprocessor, the amplifying means amplifies the voltage across the resistive mans, the microprocessor adjusts the drive signal as a function of the voltage across the resistive means.

15. A device for modulating a drive signal to drive a motor, comprising:
- a first circuit means for generating a first series of pulses at a given frequency;
- a second circuit means for generating a second series of pulses, the second series of pulses having a frequency higher than the frequency of the first series of pulses;
- a third circuit means for generating a third series of pulses, the third series of pulses having a frequency between the frequency of the first series of pulses and the second series of pulses;
- means for combining the first, second and third series of pulses to provide the drive signal, the length of the drive signal being determined by the frequency of the first series of pulses, the drive signal further including an initial pulse stage, the length of the initial pulse stage being determined by the frequency of the third series of pulses, the remainder of the length of the drive signal being a series of pulses of the same frequency as the frequency of the second series of pulses; and
- means for monitoring the power consumption of the motor, the monitoring means including transistor means connected between the combining means and the motor, resistive means connected between the transistor means and ground, and amplifying means having an input connected to the junction of the transistor means and the resistive means and an output connected to an microprocessor, the amplifying means amplifies the voltage across the resistive means, the microprocessor adjusts the drive signal as a function of the voltage across the resistive means.

16. The device of claim 15 wherein the first series of pulses is a step clock signal.

17. The device of claim 15 wherein the first circuit means for generating a step clock signal includes a divider means the input of which is an external clock signal, the output of which is the step clock signal.

18. The device of claim 15 wherein the third circuit means for generating a third series of pulses includes a divider means in communication with a counter means, the divider means having as an input the first series of pulses.

19. The device of claim 15 further including means for synchronizing the first series of pulses and the second series of pulses.

20. The device of claim 19 wherein the synchronizing means includes a divider having as an input the first series of pulses.

* * * * *